United States Patent [19]

Loebenstein et al.

[11] Patent Number: 4,520,020

[45] Date of Patent: May 28, 1985

[54] METHOD OF PREVENTING VIRUS INCREASE IN PLANTS

[75] Inventors: Gad Loebenstein, Rehovot; Abed Gera, Ramat Aviv, both of Israel

[73] Assignee: State of Israel, Ministry of Agriculture, Beit Dagan, Israel

[21] Appl. No.: 398,358

[22] Filed: Jul. 15, 1982

[30] Foreign Application Priority Data

May 13, 1982 [IL] Israel ........................................ 65765

[51] Int. Cl.$^3$ ........................ A61K 35/78; C12P 21/06
[52] U.S. Cl. ..................................... 424/197.1; 435/68
[58] Field of Search ........................... 424/197; 435/68

[56] References Cited

PUBLICATIONS

I. Sela, Adv. in Virus Res., vol. 26: 201–237, 19.
I. Sela, et al., Virol., 89: 1–6, 1978.
G. Loebenstein et al., Virol., 100: 110–115, 1980.
Sela et al., Occurrence of Artiviral Factor in Virus Infected Plants, Virol., 17: 543–548, 1962.
Sela et al., Separation of a Highly Active Anti-Viral Factor from Virus-Infected Plants, Virol., 22: 446–451, 1964.

*Primary Examiner*—Albert T. Meyers
*Assistant Examiner*—John W. Rollins, Jr.
*Attorney, Agent, or Firm*—Finnegan, Henderson, Farabow, Garrett & Dunner

[57] ABSTRACT

A method of isolating material which inhibits virus replication in plants comprising isolating protoplasts from a local lesion-responding tobacco plant having an N gene, preferably a Samsun NN tobacco plant, inoculating the protoplasts with Tobacco Mosaic Virus, and either removing the protoplasts after a predetermined amount of time and isolating the desired material from the protoplast incubation medium, or removing the virus after a predetermined amount of time and isolating the desired material from the preparation.

Also provided is a method of isolating material which inhibits virus replication in plants comprising isolating tissue from a "green island" area of a tobacco plant which responds systemically to Cucumber Mosaic Virus, preferably a Samsun NN, a Xanthi-nc or Samsun plant, homogenizing the tissue and isolating the desired material from the homogenate, as well as a method of immunizing plants against virus replication comprising applying thereto the material isolated as above.

22 Claims, 7 Drawing Figures

METHOD OF PREVENTING VIRUS INCREASE IN PLANTS

FIELD OF THE INVENTION

This invention relates to material and method for the prevention of virus increase in plants in general and, in particular, to a method for obtaining material from resistant protoplasts or tissue which prevents virus replication in plants and a method of applying this material to other plants to prevent virus replication therein.

BACKGROUND OF THE INVENTION

There exist any number of plant diseases which are caused by viruses, among them Tobacco Mosaic Virus (TMV), Cucumber Mosaic Virus (CMV), Potato Virus X (PVX) and Potato Virus Y (PVY), which cause damage to plants of commercial significance such as tobacco, tomato, sweet and bell peppers and so on. It is, therefore, desired to find a way to immunize these plants against such viruses.

Viruses spread throughout a plant in two stages. First is infection wherein the virus in introduced into the cells of the plant, and the second is replication wherein the virus muliplies within the cells of the host plant.

Plants have several natural defense mechanisms against the spread of viruses. One of these is the phenomenon of local lesion infection whereby the virus is confined to the lesion and replicates only a small group of cells around the point of entry. Another is the so-called "green islands" phenomenon, an uneven distribution of virus often seen in plants having systemic infection. These are dark green areas which generally contain little or no virus and are often resistant to reinfection. The mechanisms of these defense mechanisms are not understood.

Methods of preventing virus increase in plants in use today are generally aimed at the first stage of virus development, that is, preventing infection of the plant. Thus, there are on the market many materials which, when mixed with purified solutions of virus, prevent infection when applied to other plants. Other chemicals, for example, nucleic acid analogues, and inhibitors of nucleic acid or protein synthesis, are available which inhibit the replication of viruses in the laboratory but these have phytotoxic effects which have a significant detrimental effect on the plants as well as on the viruses.

Thus, there exists at present no practical chemotherapeutic system for supression of virus replication in plants.

SUMMARY OF THE INVENTION

It is therefore an object of the present invention to provide a method of isolating a non-toxic material which inhibits virus replication from protoplasts and plant tissue and a method of treating plants to be immunized with this material.

There is thus provided in accordance with an embodiment of the present invention a method of isolating material which inhibits virus replication in plants comprising isolating protoplasts from a local lesion-responding tobacco plant having an N gene, inoculating the protoplasts with Tobacco Mosaic Virus, removing the protoplasts after a predetermined amount of time, and isolating the desired material from the protoplast incubation medium. In a preferred embodiment, the tobacco plant is a Samsun NN tobacco plant.

There is also provided in accordance with an embodiment of the present invention a method of isolating material which inhibits virus replication in plants comprising isolating protoplasts from a local lesion-responding tobacco plant having an N gene, inoculating the protoplasts with Tobacco Mosaic Virus, removing the virus after a predetermined amount of time, and isolating the desired material from the preparation.

There is further provided in accordance with a preferred embodiment of the invention a method of isolating material which inhibits virus replication in plants comprising removing protoplasts from a Samsun NN local lesion-responding resistant plant, inoculating the protoplasts with Tobacco Mosaic Virus, homogenizing the infected protoplasts, centrifuging the homogenate to remove the virus, and partially purifying the desired material from the supernate.

There is additionally provided a method of isolating material which inhibits virus replication in plants comprising isolating tissue from a "green island" area of a tobacco plant which responds systemically to CMV, homogenizing the tissue and isolating the desired material from the homogenate. In a preferred embodiment, the tobacco plant is a Samsun NN, a Xanthi-nc or Samsun plant.

There is further provided a method of isolating material which inhibits virus replication in plants comprising isolating protoplasts from "green islands" tissue of a tobacco plant which responds systemically to CMV, reinoculating the protoplasts with Cucumber Mosaic Virus, removing the protoplasts from the incubation medium after a predetermined amount of time, and isolating the desired material from the protoplast incubation medium. In a preferred embodiment, the tobacco plant is a Xanthi-nc, Samsum NN or Samsun tobacco plant.

There is still further provided in accordance with an embodiment of the present invention a method of immunizing plants against virus replication therein comprising applying thereto the material isolated as described above. In a preferred embodiment, the material is applied through a cut stem or by spraying the leaves.

DETAILED DESCRIPTION OF THE INVENTION

The invention will be further appreciated and understood from the following detailed description taken in conjunction with the Examples and Tables.

The present invention relates to a method of isolating material which inhibits virus replication in plants comprising: (a) isolating, from a tobacco plant, cells resistant to a virus selected from the group consisting of Tobacco Mosaic Virus and Cucumber Mosaic Virus; (b) inoculating the cells with the selected virus; and (c) after a predetermined amount of time, isolating the desired material from the preparation.

Tobacco Mosaic Virus-infected protoplasts isolated from a local lesion-responding tobacco plant having an N gene have been found to release into their incubation medium, a material which inhibits virus replication (IVR) in plants. The presence of the N gene in these tobacco plants appears to enhance the plants' defence mechanism. It is preferred to utilize protoplasts of Samsun NN tobacco plants as these seem to be the most resistant to TMV. (Attempts to elicit and recover IVR from Samsun NN protoplasts inoculated with Cucumber Mosaic Virus-6 were unsuccessful.) The IVR material released by the protoplasts has been found to inhibit the replication of virus in protoplasts of both local lesion-responding resistant tobacco plants and systemic-responding susceptible tobacco plants.

Isolation of material which inhibits replication of viruses (IVR) from the incubation medium of protoplasts according to the method of an embodiment of the present invention is described in detail in Example I. Protoplasts are obtained from Samsun NN or other suitable tobacco plant and inoculated with TMV. After incubation for a predetermined amount of time, the protoplasts are removed and the IVR material isolated from the incubation medium and partially purified using the $ZnAc_2$ method used for interferon purification. This comprises sterilizing the incubation medium through a Millipore filter, centrifuging the medium and dialyzing the supernatant against phosphate buffer. The solution is again centrifuged and $ZnAc_2$ is added to the supernatant. After 3 hours, the preparation is centrifuged, the supernatant discarded, and the precipitate dissolved with 0.02N HCl bringing the solution to pH 2.5–2.6. After centrifugation, the supernatant is dialyzed overnight against 0.01M phosphate buffer pH 6.0, and centrifuged. The precipitate is discarded and the supernatant lyophilized and kept at $-20°$ until use.

Isolation of material which inhibits replication of viruses (IVR) from protoplasts themselves according to the method of an embodiment of the present invention is described in detail in Example II. TMV-infected protoplasts are collected by centrifugation and homogenized. The homogenate is centrifuged, the precipitate discarded and the supernatant ultracentrifuged to remove the virus. The IVR is partially purified from the supernatant. It will be appreciated that IVR can also be isolated from resistant tissue of local lesion-responding tobacco plants.

Isolation of IGI (Inhibitor from Green Islands) from "green island" tissue according to the method of an embodiment of the present invention is described in Example III. Xanthi-nc or Samsun NN or other tobacco plants which respond systemically to CMV are inoculated with Cucumber Mosaic Virus. About four weeks after inoculation, "green islands" are separated from the rest of the infected leaf and the tissue homogenized. The desired IGI material is then isolated from the homogenate.

IGI material may also be isolated from the incubation medium of infected protoplasts taken from "green islands" tissue. The method of isolation is further described in Example IV. Protoplasts are isolated from "green islands" areas of tobacco plant which responds systemically to CMV, such as Xanthi-nc, Samsun NN or Samsun plants. Since these tissues already contain IGI material, they need not be further inoculated with virus. However, reinoculation serves to increase the amount of IGI released by the protoplasts.

After various predetermined amounts of time, the protoplasts are removed by centrifugation from the incubation medium. IGI is isolated from the incubation medium or it may be further purified using the $ZnAc_2$ method.

In a preferred embodiment of the invention, IGI is isolated from "green islands" tissue of Xanthi-nc plants which have been infected with Cucumber Mosaic Virus.

Inhibitory potency of IVR isolated from protoplast incubation medium according to the method of Example I was assayed on newly prepared protoplasts. The procedures and results are discussed in Example V and Tables 1 and 2.

This IVR was also employed according to an embodiment of the method of the present invention to immunize plants against virus replication. The method and results are discussed in detail in Examples VI through IX, Tables 3 to 5, and FIGS. 1 and 2.

Inhibitory potency was first assayed on leaf disks to confirm that IVR inhibits virus replication when applied to intact plant tissue. IVR was shown to inhibit replication of TMV in tobacco leaf tissue disks. The fact that IVR is neither host-specific nor virus-specific was shown by the fact that IVR inhibits TMV in leaf tissue disks of tomato plants and by the fact that IVR isolated from TMV-infected tobacco plants is active to prevent virus replication of Cucumber Mosaic Virus (CMV) in tobacco plants, cucumbers, and bell pepper leaves, as well as Potato Virus (PVX) on tobacco leaves.

One method of immunizing plants according to an embodiment of the present invention comprises applying the material isolated by any of the above methods to the cut stems of the plants to be immunized. An alternate method of immunization is to apply the material to the leaves of the plants to be immunized, as by spraying. Experimental results of these methods of immunization are described in Examples XIII and IX and accompanying FIGS. 1 and 2.

IVR isolated according to the procedure of Example II and IGI isolated according to the method of Example III were assayed to determine inhibitory potency both in protoplasts and on leaf tissue disks. Procedures and results are described in detail in Examples X through XII and Tables 2 through 10.

It is appreciated that the IVR isolated by the methods of the present invention are proteinaceous and are present in very small quantities, when present at all, in plant tissue. These IVR are resistant to low pH (i.e. pH 2.5) and retain their activity for months at low temperature ($-20°$ C.). They are resistant to degradation by RNAase and have molecular weights of approximately 26,000 and 57,000 Dalton. They are inactivated by treatment with proteolytic enzymes such as trypsin and chymotrypsin, and by heating at 60° for 10 minutes. The experimental results on which these conclusions are based are presented in Examples XIII to XV.

In a preferred embodiment of the present invention, the plants to be immunized are treated with IVR or IGI up to 18 hours after infection. It will be appreciated that application of IVR before infection will serve to inhibit both infection and replication of viruses, and leaf tissue cultures grown in IVR show resistance to infection and replication throughout their life. The effect of time of inoculation relatiave to time of infection is illustrated in Example XVI.

EXAMPLE I

Preparation of protoplasts and isolation of IVR from protoplast incubation medium Protoplasts were obtained from the two upper leaves of Nicotiana tabacum L. cv. Samsùn NN and Samsun plants, 5–6 weeks after planting. Three feedings with a complete nutrient solution were given at weekly intervals, starting 1 week after planting, and leaves 9–12 from the top were selected 10–14 days after the last feeding. The mixed enzyme procedure with overnight incubation was employed, using 0.02–0.06% Macerozyme R-10 (a registered Trade name of Yakult Biochemicals Ltd., Nishinomiya, Japan) and 0.2–0.6% Cellulase R-10 (a registered Trade name of Yakult Biochemicals Ltd., Nishinomiya, Japan) in incubation medium (VIM) containing 13.5% (w/v) mannitol. Alternatively, peeled leaf pieces were incubated in 0.03% Pectolyase Y-23 (a registered Trade name of Seishin) (Seishin Pharmaceutical Co., Nagareyama, Japan) and 0.3% Cellulase R-10 (a registered Trade name of Yakult Biochemicals Ltd., Nishinomiya, Japan) in VIM for 3–4 hours at 25° in the dark. Protoplasts were washed twice with 13.5% mannitol, floated on 23% sucrose, and again washed twice with 13.5% mannitol.

Each batch of protoplasts was divided into two lots. One, containing $5 \times 10^6$ protoplasts in 10 ml 13.5% mannitol, was inoculated with 10 ml TMV (2 µg/ml) purified by density gradient centrifugation in 0.02M potassium citrate buffer pH 5.2, containing 13.5% mannitol, and poly-L-ornithine (2 µg/ml) Sigma, approx. MW 120,000) (PLO). The second batch was sham inoculated with the same infection medium, without TMV. The two mixtures were incubated at 25° for 10 min while being rocked gently. Protoplasts were then washed twice with 13.5% mannitol containing 0.1mM $CaCl_2$, and once with VIM containing carbenicillin (200 µg/ml) and mycostatin (25 units/ml); they were then divided into 10-ml portions in 100-ml Erlenmeyer flasks at a concentration of $1 \times 10^5$ protoplasts/ml, and incubated at 25° under continuous illumination of about 2000 lx. After 72 hours the incubation media were collected and sterilized by filtration through Millipore 0.2-µm filters, after removing the protoplasts by centrifugation at 35 g for 6 minutes. The media from the inoculated and the sham-inoculated protoplasts will be termed "incubation medium" (IM) and "control medium", respectively. No. residual infectivity was detected in IM. The number of infected protoplasts was determined several times by the fluorescent antibody technique (Loebenstein et al., 1977), and found to be in the 70–80% range.

Partial purification of IVR

For parial purification of IVR the $ZnAc_2$ method used for interferon purification (Lampson et al., 1963) was employed. Incubation medium (IM) was obtained from $6 \times 10^6$ inoculated protoplasts incubated for 72 hours with 30 ml VIM in 500 ml Erlenmeyer flasks at 25°. IM was collected after removal of protoplasts, sterilized through a Millipore filter (0.2 µm), and dialyzed overnight against 0.1M glycine pH 2.5 in the cold (this step was omitted in later experiments). It was then centrifuged at 2500 g for 15 min, the precipitate discarded, and the supernatant dialyzed against 0.1M phosphate buffer pH 7.0 for 48 hours, with two changes of the buffer. The solution was then centrifuged at 3500 g for 20 minutes, the precipitate was discarded and $ZnAc_2$ was added to the supernatant to a final concentration of 0.02M. After 3 hours the preparation was centrifuged for 45 minutes at 2000 g, the supernatant discarded, and the precipitate dissolved with 0.02N HCl by bringing the solution of pH 2.5–2.6. After centrifugation for 15 minutes at 2500 g, the supernatant was dialyzed overnight against 0.01M phosphate buffer pH 6.0, and centrifuged for 15 minutes at 2500 g. The precipitate was discarded, and the supernatant lyophilized and kept at −20° until use.

EXAMPLE II

Isolation of IVR from protoplasts

To recover material which inhibits viral replication (IVR) from protoplasts themselves, $1 \times 10^7$ TMV-infected Samsun NN and control protoplasts were collected at various times after inoculation by centrifugation at 35 g for 6 minutes. Protoplasts were homogenized in 5 ml of 0.1M phosphate buffer pH 7.0 for 2.5 minutes, in the cold, with the aid of a microattachment to an Omni-Mixer. The homogenate was centrifuged at 8000 g for 10 minutes, the precipitate discarded, and the supernate ultracentrifuged at 100,000 g for 1.5 hour to remove the virus. No infectivity could be detected in the supernate. IVR was then partially purified from the supernate using precipitation by $ZnAc_2$ (the method used for interferon purification, Lampson et al, 1963).

$ZnAc_2$ was added to the supernate to a final concentration of 0.02M. After 3 hours, the preparation was centrifuged for 45 minutes at 2000 g, the supernatant discarded, and the precipitate dissolved with 0.02N HCl by bringing the solution to pH 2.5–2.6. After centrifugation for 15 minutes at 2500 g, the supernatant was dialyzed overnight against 0.01M phosphate buffer pH 6.0, and centrifuged for 15 minutes at 2500 g. The precipitate was discarded, and the supernatant lyophilized and kept at −20° until use.

EXAMPLE III

Isolation of IGI from "Green Islands" tissue

Xanthi-nc plants were inoculated with Cucumber Mosaic Virus. Four weeks after inoculation, "green islands" appeared on the leaves of the infected plants. "Green island" tissue was separated from the remainder of the infected leaf and extraction was carried out with homogenizer in 0.1M borate buffer at pH 9.0 (1:1 v/w). The extracts were centrifuged at 3500 g for 20 minutes and the precipitate discarded. The supernate was dialyzed overnight against 0.1M glycine buffer, pH 2.5, and then dialyzed back against 0.1M phosphate buffer, pH 7.0. The preparation was centrifuged for 20 minutes at 3500 g and the precipitate discarded.

IGI was then partially purified from the supernate by precipitation with 0.02M $ZnAc_2$. The preparation was centrifuged for 30 minutes at 2000 g, the supernatant discarded, and the precipitate dissolved with 0.2M HCl bringing the solution to pH 2.5–2.6. After centrifugation at 2500 g for 40 minutes, the supernatant was dialyzed overnight against 0.01M phosphate buffer, pH 6.0, and centrifuged for 15 minutes at 2500 g. The precipitate was discarded and the supernate stored until use.

EXAMPLE IV

Isolation of IGI from protoplast incubation medium

Protoplasts were obtained from "green islands" areas of Xanthi-nc, Samsun NN or Samsun tobacco plants. Some of these protoplasts were inoculated with CMV, some were inoculated with TMV and some were not inoculated at all. At various times after inoculation, the protoplasts were removed from the incubation medium by centrifugation at 35 g for 6 minutes. The supernatent was tested for inhibition of virus replication in protoplasts and a portion was further purified using the $ZnAc_2$ method described in previous Examples.

EXAMPLE V

Assay of inhibitory potency of IVR

Before testing for inhibitory potency, the partially purified IVR preparation was dissolved in 1 ml 0.01M phosphate buffer pH 6.0, dialyzed overnight against 0.1M phosphate buffer pH 6.0, centrifuged for 15 minutes at 2500 g, and then dialyzed overnight against VIM, all steps being conducted in the cold. After dialysis against VIM the preparations were diluted appropriately with VIM. Inhibitory effect was determined as described using $10^6$ protoplasts which had been inoculated 5 hours earlier, suspended in 10 ml test medium and assayed after 72 hours of incubation.

To test the potency of inhibition of virus replication in the incubation medium (IM), newly prepared Samsun and Samsun NN protoplasts were inoculated with TMV and after 5 hours or more were suspended in IM and in control medium. The protoplasts, at a concentration of $10^5$/ml in 10 ml medium, were incubated for 72 or 96 hours at 2000 lx. They were then collected by centrifugation and homogenized for 2.5 min in 4 ml of 0.05M phosphate buffer, pH 7.5, in the cold, with the aid of a microattachment to an Omni-Mixer. The homgenate was inoculated onto 12 half-leaves of N. glutinosa plants and compared with a standard solution of purified TMV on the opposite half-leaf. Lesion counts were adjusted to $10^6$ live protoplasts and calibrated.

Calibrated number of lesions per half-leaf for homogenate =

$$\frac{\text{mean number of lesions per half-leaf produced by homogenate}}{\text{mean number of lesions produced by standard TMV on opposite half-leaf} \times \text{mean number of lesions per half-leaf produced by standard TMV from all experiments}}$$

Preparations from similarly treated noninoculated protoplasts, served as controls. The $OD_{280}$ of the control and IVR preparations did not vary by more than 15%; nevertheless, control solutions were adjusted to the same $OD_{280}$ as IVR preparations.

The survival rate of the protoplasts after 96 hours was generally around 90%, and those experiments with survival rates lower than 80% were discarded. In some samples virus titer in the protoplast homogenate was also determined by enzyme-linked immunosorbent assay (ELISA) (Clark and Adams, 1977), calibrated to purified TMV.

Results

The results as to inhibitory potency of IVR material released into the incubation medium from TMV-infected protoplasts of resistant Samsun NN plants are shown in Table 1.

Crude IVR consistently inhibited virus replication in protoplasts from both resistant (Samsun NN) and susceptible (Samsun) plants by about 60%, as measured by local lesion infectivity assay on N. glutinosa, and 70-90% as measured by ELISA. Incubation medium from inoculated Samsun (susceptible) protoplasts did not inhibit TMV replication in either Samsun NN or Samsun protoplasts (Table 2).

TABLE 2

EFFECT OF INCUBATION MEDIUM (IM) FROM SAMSUN PROTOPLASTS (SUSCEPTIBLE) ON VIRUS REPLICATION IN SAMSUN NN AND SAMSUN PROTOPLASTS[a]

| Test protoplasts | Hours of incubation | Infectivity[b] Protoplasts in IM | Protoplasts in control medium[c] | Infectivity from control protoplasts[d] |
|---|---|---|---|---|
| Samsun NN | 48 | 13.0 ± 0.41 | 13.6 ± 3.9 | 11.9 |
| | 72 | 29.6 ± 3.5 | 33.1 ± 0.9 | 29.8 |
| | 96 | 36.8 ± 5.7 | 37.8 ± 4.0 | 36.1 |
| Samsun | 48 | 25.4 ± 9.41 | 21.8 ± 4.37 | 28.5 |
| | 72 | 45.6 ± 20.52 | 43.8 ± 12.1 | 45.5 |
| | 96 | 47.9 ± 11.77 | 46.6 ± 11.97 | 49.2 |

[a]Average of three to four experiments.
[b]Average number of local lesions and standard error per $10^6$ protoplasts on one half-leaf of N. glutinosa, calibrated to standard TMV solution (2.5 μg/ml) which yielded about 60 lesions per half-leaf.
[c]Medium in which uninoculated protoplasts were suspended.
[d]Protoplasts without change of incubation medium.

Crude IVR also inhibited virus replication in Samsun NN protoplasts at dilutions of 1:5 and 1:10, but not at 1:20, with an average inhibition of 49 and 42%, respectively.

IVR could be detected as soon as 24 hours after inoculation of the protoplasts, though levels of activity were low. Thus, when IVR was sampled after 24 and 48 hours and applied to Samsun NN test protoplasts for 96 hours, inhibition reached 19.5 and 30.5% (average from two experiments), respectively, compared to about 60% when samples 72 hours after inoculation.

TABLE 1

EFFECT OF INHIBITORY SUBSTANCE(S) (IVR) IN INCUBATION MEDIUM FROM SAMSUN NN PROTOPLASTS (RESISTANT) ON VIRUS REPLICATION IN SAMSUN NN AND SAMSUN PROTOPLASTS[a]

| Test protoplasts | Hours of incubation | Infectivity[b] Protoplasts in IVR | Protoplasts in control medium[c] | Percentage inhibition of infectivity | Virus yield[d] (μg/$10^6$ protoplasts) Protoplasts in IVR | Protoplasts in control medium[c] | Percentage reduction of virus yield | Control protoplasts[e] Infectivity | Virus yield[d] (μg/$10^6$ protoplasts) |
|---|---|---|---|---|---|---|---|---|---|
| Samsun NN | 48 | 1.3 ± 1.11 | 11.3 ± 2.99 | 62 | <0.01 | 0.05 | >80 | 9.6 | 0.04 |
| | 72 | 8.6 ± 3.5 | 24.6 ± 8.0 | 58 | 0.05 | 3.2 | 98 | 23.6 | 2.8 |
| | 96 | 15.3 ± 1.45 | 35.5 ± 1.68 | 57 | 2.0 | 6.8 | 71 | 32.7 | 3.6 |
| Samsun | 48 | 7.3 ± 2.71 | 17.2 ± 6.27 | 58 | | | | 21.4 | |
| | 72 | 14.1 ± 4.5 | 34.1 ± 6.93 | 59 | 1.9 | 6.0 | 68 | 41.1 | 4.8 |
| | 96 | 18.9 ± 4.7 | 49.8 ± 11.32 | 62 | 1.9 | 20.0 | 90 | 47.2 | 28.0 |

[a]Average of four to eight experiments.
[b]Average number of local lesions and standard error per $10^6$ protoplasts on one half-leaf on N. glutinosa, normalized to a standard TMV solution (2.5 μg/ml) which yielded about 60 lesions per half-leaf.
[c]Medium in which uninoculated protoplasts were suspended.
[d]As determined by ELISA.
[e]Protoplasts without change of incubation medium.

EXAMPLE VI

Inhibition of virus replication by IVR in leaf disks

Samsun tobacco plants were inoculated with a 2.5 µg/ml solution of purified TMV and kept in the greenhouse. Five hours later, disks 11 mm in diameter were cut from the inoculated leaves, and floated on IVR and control preparations (partially purified by $ZnAc_2$ precipitation), dissolved in incubation medium (VIM) (without mannitol) in 5-cm petri dishes. Disks were incubated at 25° C. under continuous illumination. After various times of incubation, two disks from each IVR and control test were sampled, washed with distilled water, and homogenized in 2 ml 0.05M phosphate buffer pH 7.5. The homogenate was inoculated onto 12 half-leaves of *N. glutinosa* plants and compared with a standard solution of purified TMV on the opposite half-leaf. Lesion counts after 48 to 96 hours were calibrated, as described previously.

In several samples, virus titer was also determined by ELISA (enzyme-linked immunosorbent assay, Clark and Adams, 1977).

Results

Floating disks 5 hours after their inoculation on one unit of IVR (IVR obtained from $10^6$ protoplasts, incubated for 72 hours after their inoculation) reduced virus replication by 60–90%, as determined by both local lesion assay and ELISA (Table 3). No difference in virus titers was observed between that in disks floated on control medium ($ZnAc_2$ preparations from non-inoculated protoplasts in VIM) and that from disks floated on VIM only. Inhibitory activity rose with increasing concentrations of IVR. Thus, 0.5, 1, 3, 5, and 10 units inhibited TMV replication in disks by 54, 56, 67, 75 and 84% respectively, as determined by local lesion assay 72 hours after inoculation. IVR (one unit) applied to leaf disks 8 hours after their inoculation with TMV reduced virus replication by 55–65%, as determined by local lesion assay.

EXAMPLE VIII

Inhibition of other viruses by IVR

For evaluation of IVR against Cucumber Mosaic Virus (CMV), and Potato Virus X (PVX), Samsun NN, cucumber cv. 'Bet Alpha' and bell pepper cv. 'Vinedale' plants were inoculated with CMV, and *N.glutinosa* plants with PVX. Plants were kept in the greenhouse, and disks were removed from inoculated leaves and floated on IVR and control preparations as described above. CMV infectivity was assayed on *Vigna sinensis* Endl. cv. 'Blackeye', and PVX on *Gomphrena globosa* L. plants, comparing IVR and control treatments on opposite leaves.

Results

IVR was active against viruses other than TMV when tested in leaf disks of several hosts. IVR inhibited CMV in leaf disks of Samsun NN and cucumbers. Inhibition rates, by one unit of IVR, ranged between 60 and 80% when assayed up to 120 hours after inoculation. (Table 4). Similar results were obtained with bell pepper leaf disks, with inhibition rates of 63, 69 and 64% when assayed 48, 72 and 96 hours respectively after inoculation with CMV IVR also reduced replication of PVX in *N.glutinosa* leaf disks, with inhibition rates (by one unit of IVR) between 60 and 70% (Table 5).

EXAMPLE VIII

Application of IVR through cut stems

Two developed leaves of Samsun tobacco plants, 4 to 5 weeks after transplanting, were inoculated with TMV (2.5 µg/ml). After 5 hours, stems were cut about 2 cm above the soil, and plants were placed in vials containing IVR (one unit dissolved in 5 ml of distilled water) or control preparations for 3 hours for the solution to be taken up. Plants were then transferred to flasks with distilled water, and kept at 25° C. under continuous illumination. After various time intervals, two 11 mm disks were sampled from inoculated leaves and assayed as described.

Results

Figure 1A:
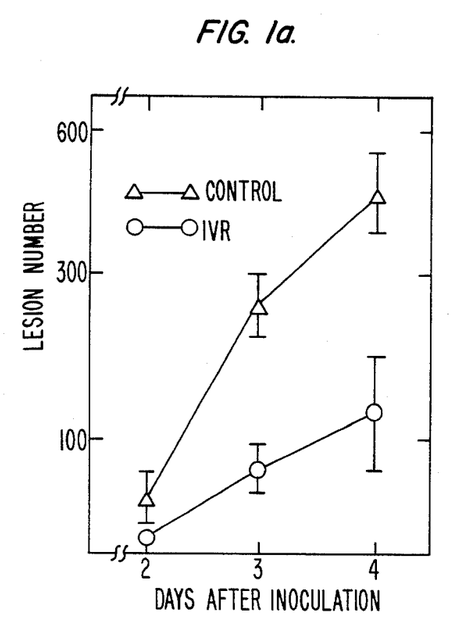
Figure 1B:
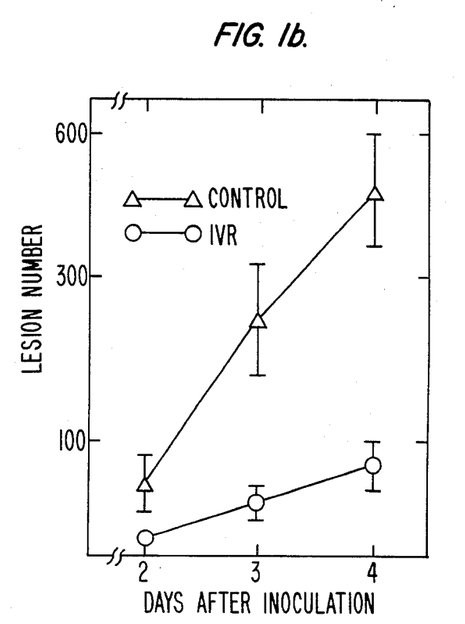
Figure 2A:
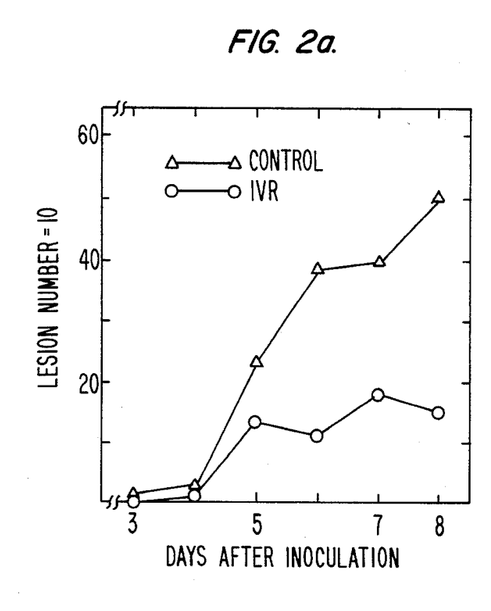
Figure 2B:
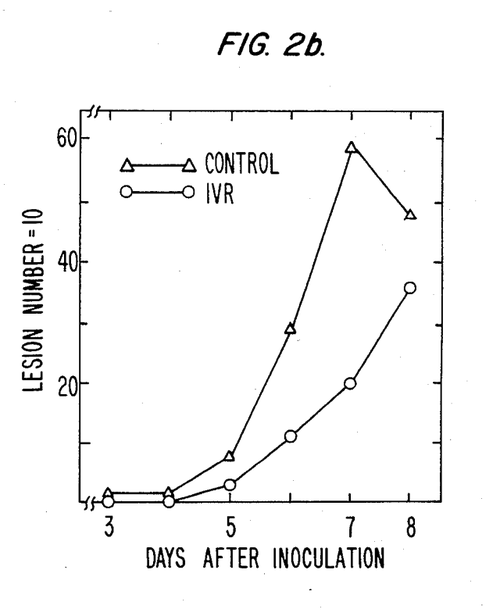
Figure 2C:
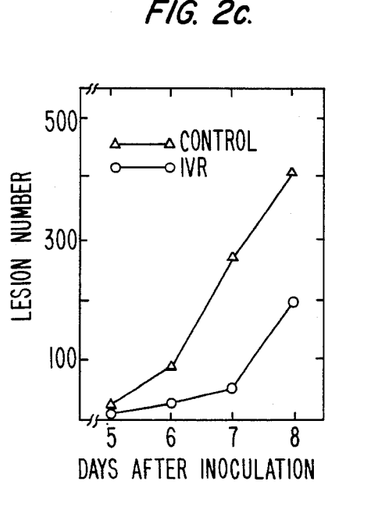
Figure 2D:
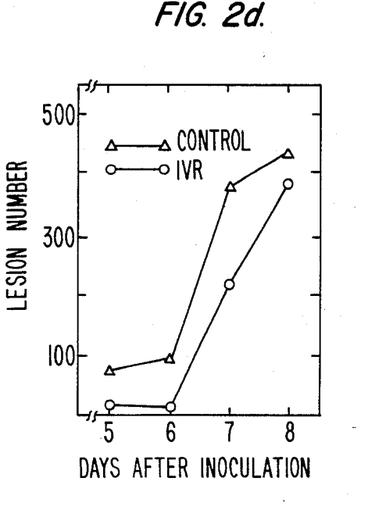

Application of IVR through cut stems of Samsun plants 2 hours before (a) or 5 hours after (b) inoculation reduced extractable TMV by about 80 and 70% respectively. FIG. 1 shows the average number of local lesions ± standard error on one half leaf of *N.glutinosa* from 4 experiments.

TABLE 3

Effect of IVR on TMV replication in Samsun leaf tissues disk[a].

| Hours after inoculation | Infectivity[b] Disks floated on | | % Inhibition of Infectivity | Virus yield[d] Disks floated on | | % Reduction of virus yield | Control disks[e] | |
|---|---|---|---|---|---|---|---|---|
| | IVR | Control medium[c] | | IVR | Control medium[c] | | Infectivity[b] | Virus yield[d] |
| 24 | 7.4 ± 4.2 | 36.2 ± 9.1 | 80 | 0.06 ± 0.05 | 0.96 ± 0.42 | 94 | 36.2 | 0.67 |
| 48 | 57.2 ± 5.7 | 234 ± 84 | 76 | 0.46 ± 0.34 | 2.3 ± 0.26 | 80 | 240.7 | 3.0 |
| 72 | 387.5 ± 65.9[f] | 1660 ± 103.9[f] | 77 | 5.85 ± 1.25 | 43.35 ± 10.45 | 87 | 1261[f] | 31.5 |
| 96 | 1997 ± 403[f] | 14000 ± 869[f] | 86 | 66.0 ± 8.85 | 367.5 ± 31.8 | 82 | 16300[f] | 430 |
| 120 | 6660 ± 56.7[f] | 19075 ± 1873[f] | 65 | 153.5 ± 3.5 | 497.5 ± 53.0 | 69 | 18300[f] | 480 |

[a]Average of 3–5 experiments.
[b]Average number of local lesions ± standard error on one half-leaf of *N. glutinosa*
[c]ZnAc₂ preparation from medium in which non-inoculated protoplasts were suspended.
[d]Average yield (µg/disk) ± standard error, as determined by ELISA.
[e]Disks floated on VIM solution.
[f]Homogenate was diluted 10-fold or 100-fold. The average number of lesions on 12 half-leaves induced by the appropriate dilution was multiplied by the dilution factor.

Inhibition of TMV replication by IVR was also assayed on tomato plant tissue disks using the same method. The results show that IVR is also active against TMV replication in host plants other than tobacco plants.

One unit of IVR inhibited replication of TMV by 64, 62 and 72% respectively when assayed 48, 72 and 96 hours after inoculation of tomato plant tissue disks.

TABLE 4

Effect of IVR on replication of cucumber mosaic virus in cucumber and Samsun NN leaf tissue disks[a].

| Hours after inoculation | Infectivity[b] Disks floated on IVR | Infectivity[b] Disks floated on Control medium[c] | % Inhibition of infectivity | Virus yield[d] Disks floated on IVR | Virus yield[d] Disks floated on Control medium[c] | % Reduction of virus yield | Control disks[e] Infectivity | Control disks[e] Virus yield[d] |
|---|---|---|---|---|---|---|---|---|
| Samsun NN | | | | | | | | |
| 48 | 36.7 ± 12.9 | 111.7 ± 28.5 | 67 | 0.7 ± 0.1 | 2.1 ± 0.7 | 67 | 88 | 1.75 |
| 72 | 257 ± 41.0[f] | 958 ± 174[f] | 73 | 4.4 ± 0.95 | 18.0 ± 5.3 | 76 | 807[f] | 16.0 |
| 96 | 1034 ± 120.4[f] | 4690 ± 208[f] | 78 | 30.5 ± 4.3 | 88.3 ± 9.4 | 65 | 4200[f] | 80 |
| 120 | 1110 ± 42.2[f] | 5065 ± 226[f] | 78 | 27.5 ± 3.5 | 97.5 ± 5.3 | 72 | 6000[f] | 115 |
| Cucumber | | | | | | | | |
| 48 | 14.4 ± 0.75 | 65.2 ± 17.8 | 78 | 0.28 ± 0.03 | 1.33 ± 0.39 | 79 | 55.5 | 1.13 |
| 72 | 166 ± 26.2[f] | 411 ± 51.6[f] | 60 | 3.37 ± 0.88 | 8.0 ± 1.41 | 58 | 455[f] | 8.5 |
| 96 | 896 ± 82.5[f] | 2008 ± 15.9[f] | 65 | 11.3 ± 2.4 | 35 ± 3.07 | 68 | 2166[f] | 39.5 |
| 120 | 1355 ± 59.4[f] | 4280 ± 305[f] | 68 | 27.5 ± 3.5 | 80 ± 14.4 | 65 | 4340[f] | 84.0 |

[a]Average of 3–4 experiments.
[b]Average number of local lesions ± standard error on one leaf of *V. ginensis* plants.
[c,d,e]See Table 1.

TABLE 5

Effect of IVR on replication of potato virus X in *N. glutinosa* leaf tissue disks[a]

| Hours after inocu- lation | Infectivity[b] Disks floated on IVR | Infectivity[b] Disks floated on Control medium[c] | % Inhibi- tion of infec- tivity | Infectivity from control disks floated on VIM |
|---|---|---|---|---|
| 48 | 32 ± 15.3 | 100 ± 15.8 | 68 | 112 |
| 72 | 98 ± 13.0 | 331 ± 85.8 | 70 | 471 |
| 96 | 1176 ± 33.2[f] | 3331 ± 292.8[f] | 65 | 3620[f] |

[a]Average of two experiments.
[b]Number of local lesions ± standard error per *G. globosa* leaf; average from 12 leaves.
[c]See Table 1.

EXAMPLE IX

Application of IVR by spraying

Spray applications of IVR (3 units in 10 ml distilled water) and control preparations were made to the upper side of the leaves of Samsun plants (3 weeks after transplanting) 5 hours after their inoculation with TMV (2.5 µg/ml) on their lower side. TMV was assayed after various times from both inoculated and non-inoculated leaves.

Results

Spraying intact plants with IVR 2 hours before or 5 hours after inoculation and assaying 7 days after inoculation gave inhibition rates of about 78% and 56% respectively when inoculated leaves were assayed. In non-inoculated leaves, one spray gave inhibition rates of 81% and 43% respectively. FIG. 2 illustrates TMV replication of Samsun plants sprayed with IVR (3 units) and control preparation 2 hours before inoculation, when inoculated (a) and non-inoculated (b) leaves were assayed; and virus replication in plants sprayed with IVR and control preparation 5 hours after inoculation, when inoculated (c) and non-inoculated (d) leaves were assayed. Average number of local lesion on one half leaf of *N.glutinosa* from 2 experiments is shown.

Assays 8 days after inoculation generally gave lower rates of inhibition, perhaps due to degradation and/or dilution of IVR in the plant.

EXAMPLE X

Inhibition of virus replication by IVR from protoplasts in leaf disks

Samsun tobacco plants were inoculated with TMV according to the method described in Example III and leaf disks floated on IVR isolated according to the method of Example I and control preparations.

Results

This IVR reduced TMV multiplication in leaf disks by 78–85% compared with the controls. (Table 6).

TABLE 6

Effect of IVR isolated from inoculated Samsun NN protoplasts, on TMV replication in Samsun leaf tissue disks[a].

| Hours after inocu- lation | Infectivity[b] Disks floated on IVR | Infectivity[b] Disks floated on Control medium[c] | % Inhibi- tion of Infec- tivity | Infectivity[b] from control disks[e] |
|---|---|---|---|---|
| 24 | 6.5 ± 0.70 | 29.3 ± 3.05 | 78 | 30.7 ± 3.06 |
| 48 | 35.3 ± 6.11 | 159.3 ± 19.0 | 778 | 147.3 ± 20.03 |
| 72 | 252 ± 37.47[f] | 1133 ± 80.21[f] | 78 | 1218 ± 107.7[f] |
| 96 | 1920 ± 262.3[f] | 12733 ± 002[f] | 85 | 12633 ± 1274[f] |

[a]Average of three experiments.
[b]Average number of local lesions ± standard error on one half-leaf of *R. glutinosa*.
[c,e]See Table 1.

EXAMPLE XI

Inhibition of virus replication by IGI

The inhibitory effect of IGI isolated from "green islands" tissue according to the method of Example III was tested in isolated protoplasts from Samsun, Samsun NN and Xanthi-nc plants.

Newly prepared Samsun and Samsun NN protoplasts were inoculated with TMV and, after five hours or more, were suspended in IGI and in control medium. The protoplasts, at a concentration of 10⁵/ml in 10 ml medium, were incubated for 72 and 96 hours at 2000 lx. They were then collected by centrifugation and homogenized for 2.5 minutes in 4 ml of 0.05M phosphate buffer, pH 7.5, in the cold, with the aid of a microattachment to an Omni-Mixer. The homogenate was inoculated onto 12 half-leaves of *N.glutinosa* plants and compared with a standard solution of purified TMV on the opposite half-leaf. Lesion counts were adjusted to $10^6$ live protoplasts and calibrated as described previously.

Results

Assaying Samsun protoplasts 24, 48 and 72 hours after inoculation gave inhibition rates of 52, 59 and 57% respectively (Table 7). Assaying Samsun NN protoplasts 48 and 72 hours after inoculation gave inhibition rates of 70 and 61% respectively (Table 8).

EXAMPLE XII

Inhibition of virus replication by IGI from incubation medium

The inhibitory effect of IGI isolated from the "green islands" protoplast incubation medium according to the method of Example IV was tested in isolated protoplasts from Samsun and Xanthi-nc plants.

Newly prepared Samsun and Xanthi-nc protoplasts were inoculated with CMV and, after five hours or more, were suspended in IGI and control preparations. After various incubation times, infectivity was assayed.

Results

Assaying Xanthi-nc protoplasts infected with CMV 48 hours after inoculation gave inhibition rates of 50–70% as shown in Table 9. Similar results were obtained on TMV-infected Samsun and Samsun NN protoplasts with inhibition rates of 70 and 80% respectively.

TABLE 7

Effect of IGI on TMV Replication in Samsun Protoplasts.

| Hours after Inoculation | Protoplast in IGI | Protoplasts in Control Medium | Inhibition % |
|---|---|---|---|
| 24 | 9.6* | 19.8 | 52 |
| 48 | 19.1 | 46.3 | 59 |
| 72 | 26.1 | 61.2 | 57 |

*Average number of lesions per *N. glutinosa* half leaf.

TABLE 8

Effect of IGI isolated from intact "green islands" tissue on TMV replication in Samsun NN protoplasts

| | Infectivity* | | |
|---|---|---|---|
| Hours after inoculation | Protoplasts in IGI | Protoplasts in control medium | Inhibition % |
| 48 | 4.0 | 13.3 | 70 |
| 72 | 15.3 | 39 | 61 |

*Average number of lesions per *N. glutinosa* half leaf.

TABLE 9

Effect of IGI from Protoplasts Superinfected with CMV on CMV Replication in Xanthi-nc Protoplasts

| | Lesion* Number | Inhibition % |
|---|---|---|
| Protoplast in Control Medium | 19.2 | |
| Protoplasts in IGI isolated from non-infected Protoplasts | 9.8 | 69 |
| Protoplasts in IGI isolated from CMV Superinfected Protoplasts | 6 | 49 |

*Average Number of Lesions per Cowpea Half Leaf.

EXAMPLE XIII

Molecular weight estimation of IVR

A preliminary estimation of the molecular weight of IVR was obtained by gel filtration of Sephadex G-75 (Superfine, Pharmacia) (Whitaker, 1963). A 33×2.3-cm column calibrated with cytochrome c, RNAase A, chymotrypsinogen A, Ovalbumin, and bovine serum albumin was used. A lyophilized $ZnAc_2$ preparation, obtained from $3 \times 10^7$ inoculated protoplasts, was dissolved in 1 ml of 0.1M phosphate buffer, pH 6.0 ($OD_{280}=2$), placed on the column, and eluted with the same buffer at a flow rate of 100 ml/hr. Fractions of 1 ml each were collected. A control preparation obtained from a similar number of noninoculated protoplasts, with the $OD_{280}$ adjusted to 2, was passed through the same column and collected in a similar way. Interference potency of each third fraction, in comparison with the respective control fraction, was tested as before on inoculated Samsun NN protoplasts, after dialysis overnight against VIM.

Results

Figure 3:
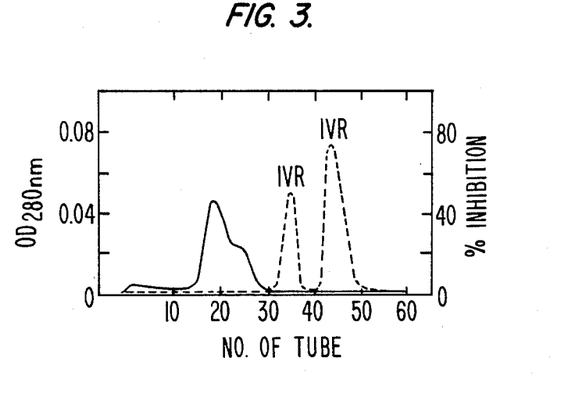

Peaks of activity were eluted at two positions, equivalent to molecular weights of 26,000 and 57,000 (FIG. 3). In a parallel experiment, when 2 ml of lyophilized $ZnAc_2$ preparation obtained from $6 \times 10^7$ inoculated protoplasts was placed on the same column, peaks of activity (74 and 37% inhibition) were eluted at positions equivalent to molecular weights of 27,000 and 56,000, respectively.

EXAMPLE XIV

Treatment of IVR with enzymes

Gel-bound trypsin (Tryspin-30, Enzygell, E.C. 2.4.214) and chymotrypsin (Enzygell, E.C. 3.4.21.1) from Bohringer, Mannheim, were suspended in 0.05M phosphate buffer pH 7.5, and RNAase (Enzyte Agarose Ribonuclease I, 36-512 Miles Biochemicals) in 0.1M acetate buffer pH 6, and washed by centrifugation to remove the non-bound fraction. Suspensions of gel-bound trypsin, chymotrypsin, and RNAase were each added to IVR (3 units in 0.5 ml) and control preparations to final concentrations of 1000, 100 and 10 g/ml respectively. After incubation for 3 hours at 25° C., enzymes were removed by centrifugation and IVR activity was assayed on tobacco protoplasts or leaf disks inoculated 5 hours previously with TMV. Protoplasts were assayed 72 hours after inoculation and leaf disks after 48 and 72 hours.

Results

Incubation of IVR with trypsin or chymotrypsin either inactivated IVR completely or reduced its activity markedly with IVR being assayed on infected protoplasts or leaf disks. When assayed on TMV-infected protoplasts, IVR reduced virus multiplication (measured by local lesion assay 72 hours after inoculation) by 68% while trypsin-treated and chymotrypsin-treated IVR gave 5 and 8% inhibition, respectively, compared with the control preparation treated similarly with the enzymes. No differences in virus titers were observed between protoplasts treated with control preparations incubated with the enzymes and those incubated without the enzymes. Trypsin and chymotrypsin inactivated by heating the enzyme for 15 minutes at 100° C. did not reduce IVR activity. Similar results were obtained when IVR was assayed on TMV-infected leaf disks (Table 10).

RNAase did not affect IVR activity when assayed on protoplasts or on leaf disks. Inhibitory activities of IVR treated with RNAase, inactivated RNAase (by adding 1mM Aurintricarboxylic acid (ATA)), and non-treated IVR, were 74, 76 and 83% respectively when assayed on leaf disks 48 hours after inoculation. Similar results were obtained when IVR activity was assayed on protoplasts.

TABLE 10

Effect of trypsin and chymotrypsin treatments on IVR activity tested on infected Samsun leaf tissue[a].

| Treatment | Infectivity[b] 48 hr after inoculation | | % Inhibition of infectivity | Infectivity[b] 72 hr after inoculation | | % Inhibition of infectivity |
|---|---|---|---|---|---|---|
| | IVR | Control preparation | | IVR | Control preparation | |
| with trypsin | 105 | 111 | 5 | 314 | 337 | 7 |
| without trypsin | 24.5 | 117 | 79 | 63.5 | 312.5 | 80 |
| inactivated trypsin | 24.5 | 122 | 80 | 77 | 322 | 76 |
| trypsin alone | | 92.5 | | | 329 | |
| with chymotrypsin | 92.5 | 94.5 | 2 | 347 | 375 | 7 |
| inactivated chymotrypsin | 36 | 118 | 69 | 125 | 373 | 66 |
| chymotrypsin alone | | 97.5 | | | 393 | |

[a]Average of two experiments.
[b]Number of local lesions per *N. glutinosa* half-leaf; average from 12 half-leaves.

EXAMPLE XV

Heat treatment of IVR

IVR (2 units) and control preparations were suspended in 0.5 ml virus incubation medium (VIM), and heated at 40°, 50°, 60° and 80° C. in thin-walled glass tubes for 10 minutes. The tubes were then cooled quickly, and IVR activity was assayed on TMV-inoculated protoplasts and leaf disks.

Results

IVR was inactivated by heating at 60° C. for 10 minutes. Heating the IVR preparation for 10 minutes, at 40°, 50°, 60° and 80° C. resulted in inhibition rates of 70, 72, 6 and 0% respectively, compared with 68% from the non-heated preparation, when assayed on TMV-infected leaf disks.

EXAMPLE XVI

Evaluation of IVR on TMV in vitro, and when applied at different times after inoculation of protoplasts Mixing IVR (3 units) with purified TMV (2.5 μg/ml) and incubating the mixture for 1 hour did not affect infectivity, when TMV was recovered by ultracentrifugation.

In the foregoing experiments, infected protoplasts were suspended in crude IVR 5 hours after inoculation with TMV. To see whether IVR is still effective when applied after a longer time interval, Samsun NN and Samsun protoplasts were inoculated with TMV and then suspended in IM from Samsun NN after 4, 12, 18 and 24 hr.

Results

Crude IVR inhibited virus replication when applied to inoculated Samsun NN protoplasts after 4, 12 and 18 hours, resulting in 58, 62, and 61% inhibition, respectively. When IVR was applied 24 hours after inoculation the effect was negligible. Similar results were obtained with Samsun protoplasts, giving inhibition rates of 61, 64, 67 and 19% respectively, when IVR was added 4, 12, 18 and 24 hours after inoculation. Application of IVR 1 hour after inoculation increased inhibition to 75%.

IVR also had no effect on mature infections of TMV and CMV. When disks from Samsun tobacco leaves, infected for 10 days with TMV, were floated for 48 hours on IVR (3 units), control preparations and VIM (without mannitol), and assayed on *N.glutinosa*, the average number of lesions per half-leaf was 371, 363 and 387 respectively. Assay of infectivity after 120 hours of floating on the test solution resulted in 398, 373 and 392 lesions respectively. Similar results were obtained with disks from cucumber leaves, infected for 10 days with CMV. The average number of lesions per cowpea leaf was 68, 65 and 79 respectively, when disks were floated for 48 hours on IVR, control preparation or VIM. Assay of infectivity after 120 hours of floating resulted in 109, 102 and 81 lesions, respectively.

It will be appreciated by those skilled in the art that the present invention is not limited by what has been specifically shown and described hereinabove and in the Examples. Rather, the scope of the invention is limited solely by the claims which follow:

We claim:

1. A method of isolating a material which inhibits replication of TMV, CMV and PVX comprising the steps of:
   - isolating protoplasts of a plant of the genus *Nicotiana tabacum* L. having an N gene;
   - inoculating the protoplasts with Tobacco Mosaic Virus;
   - incubating the inoculated protoplasts under continuous illumination for between 24 and 96 hours;
   - removing the protoplasts from the incubation medium; and
   - sterilizing the incubation medium.

2. The method of claim 1 wherein said step of isolating protoplasts comprises the steps of:
   - incubating leaf portions of a plant of the genus *Nicotiana tabacum* L. having an N gene with pectinolytic and cellulolytic enzymes to produce protoplasts;
   - washing the protoplasts with mannitol;
   - floating the washed protoplasts on 23% sucrose; and
   - washing the floated protoplasts with mannitol.

3. The method of claim 1 wherein said incubating step comprises incubating said protoplasts for 72 hours.

4. The method of claim 1 further including, following the step of sterilizing, the steps of:
   - adding $ZnAc_2$ to the sterilized supernatant to a final concentration of 0.02M;
   - after about three hours, centrifuging the solution;
   - dissolving the precipitate by bringing the solution to between pH 2.5–2.6;
   - centrifuging the solution; and
   - dialyzing the supernatant against phosphate buffer.

5. The method of claim 4 further including the step of lyophilizing the supernatant after said step of dialyzing.

6. The method of claim 1 wherein said step of isolating protoplasts comprises the step of isolating protoplasts from a plant selected from the group consisting of *Nicotiana tabacum* L. cv. Samsun NN and *Nicotiana tabacum* L. cv. Xanthi-nc.

7. A method of isolating a material which inhibits replication of TMV, CMV and PVX comprising the steps of:
  isolating protoplasts of a plant of the genus *Nicotiana tabacum* L. having an N gene;
  inoculating the protoplasts with Tobacco Mosaic Virus;
  incubating the inoculated protoplasts under continuous illumination for between 24 and 96 hours;
  removing the protoplasts from the incubation medium;
  homogenizing the removed protoplasts in phosphate buffer;
  centrifuging the homogenate; and
  ultracentrifuging the supernate to remove the Tobacco Mosaic Virus.

8. A method of isolating a material which inhibits replication of TMV, CMV and PVX comprising the steps of:
  inoculating with Cucumber Mosaic Virus a plant of the genus *Nicotiana tabacum* L. which responds systemically to Cucumber Mosaic Virus;
  after about four weeks, separating "green islands" tissue from the remainder of the leaf;
  homogenizing the "green islands" tissue;
  centrifuging the homogenate;
  dialyzing the supernate against phosphate buffer;
  adding $ZnAc_2$ to the dialyzed supernate to a final concentration of 0.02M;
  after about three hours, centrifuging the solution;
  dissolving the precipitate by bringing the solution to between pH 2.5–2.6;
  centrifuging the solution; and
  dialyzing the supernate against phosphate buffer.

9. A method according to claim 8 and wherein said step of inoculating a plant comprises the step of inoculating a plant selected from the group consisting of *Nicotiana tabacum* L. cv. Xanthi-nc, *Nicotiana tabacum* L. cv. Samsun NN and *Nicotiana tabacum* L. cv. Samsun.

10. A method of isolating a material which inhibits replication of TMV, CMV and PVX comprising the steps of:
  inoculating with Cucumber Mosaic Virus a plant of the genus *Nicotiana tabacum* L. which responds systemically to Cucumber Mosaic Virus;
  after about four weeks, separating "green islands" tissue from the remainder of the leaf;
  isolating protoplasts from said "green islands" tissue;
  inoculating the protoplasts with a virus selected from the group consisting of Tobacco Mosaic Virus and Cucumber Mosaic Virus;
  incubating the inoculated protoplasts under continuous illumination for between 24 and 96 hours;
  removing the protoplasts from the incubation medium; and
  sterilizing the incubation medium.

11. A method according to claim 10 wherein said step of isolating protoplasts comprises the steps of:
  incubating said tissue with pectinolytic and cellulolytic enzymes to produce protoplasts;
  washing the protoplasts with mannitol;
  floating the washed protoplasts on 23% sucrose; and
  washing the floated protoplasts with mannitol.

12. A method according to claim 10 wherein said step of inoculating a plant comprises the step of inoculating a *Nicotiana tabacum* L. cv. Xanthi-nc plant and said step of inoculating the protoplasts comprises inoculating said protoplasts with Cucumber Mosaic Virus.

13. A method of immunizing a plant susceptible to TMV, CMV and PVX against the replication of any of said viruses comprising the step of introducing material isolated according to the method of either claim 1 or claim 5 into the plant.

14. The method of claim 13 wherein said step of introducing comprises introducing said material between about 5 and about 12 hours after infection of the plant by said virus.

15. The method of claim 13 wherein said step of introducing comprises the step of introducing the material through a cut stem of the plant to be immunized.

16. The method of claim 13 wherein said step of introducing comprises the step of spraying the material onto the leaves of the plant to be immunized.

17. The method of claim 13 wherein said plant is selected from the group consisting of tobacco, cucumber, sweet and bell pepper, and tomato plants.

18. A method of immunizing a plant susceptible to TMV, CMV and PVX against the replication of said viruses comprising the step of introducing material isolated according to the method of claim 8 into the plant.

19. The method of claim 18 wherein said step of introducing comprises introducing said material between about 5 and about 12 hours after infection of the plant by said virus.

20. The method of claim 18 wherein said step of introducing comprises the step of introducing the material through a cut stem of the plant to be immunized.

21. The method of claim 18 wherein said step of introducing comprises the step of spraying the material onto the leaves of the plant to be immunized.

22. The method of claim 18 wherein said plant is selected from the group consisting of tobacco, cucumber, sweet and bell pepper, and tomato plants.

* * * * *